US010682112B2

(12) United States Patent
Pizaine et al.

(10) Patent No.: US 10,682,112 B2
(45) Date of Patent: Jun. 16, 2020

(54) SUPPRESSION OF INDEPENDENT MOVEMENTS IN A SERIES OF 2D X-RAY FLUOROSCOPY IMAGES USING A 3D PRE-OPERATIVE VOLUME

(71) Applicant: KONINKLIJKE PHILIPS N.V., Eindhoven (NL)

(72) Inventors: Guilaume Julien Joseph Pizaine, Suresnes (FR); Pascal Yves Francois Cathier, Suresnes (FR); Olivier Pierre Nempont, Suresnes (FR); Raoul Florent, Suresnes (FR)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 669 days.

(21) Appl. No.: 15/037,801

(22) PCT Filed: Nov. 19, 2014

(86) PCT No.: PCT/EP2014/074966
§ 371 (c)(1),
(2) Date: May 19, 2016

(87) PCT Pub. No.: WO2015/075047
PCT Pub. Date: May 28, 2015

(65) Prior Publication Data
US 2016/0302757 A1    Oct. 20, 2016

(30) Foreign Application Priority Data

Nov. 20, 2013  (EP) ..................................... 13306585

(51) Int. Cl.
*A61B 6/00*    (2006.01)
(52) U.S. Cl.
CPC .......... *A61B 6/5264* (2013.01); *A61B 6/4441* (2013.01); *A61B 6/461* (2013.01);
(Continued)

(58) Field of Classification Search
CPC ..... A61B 6/5264; A61B 6/461; A61B 6/4441; A61B 6/5205; A61B 6/5241; A61B 6/487; A61B 6/504; A61B 6/5252
See application file for complete search history.

(56) References Cited

U.S. PATENT DOCUMENTS

| 2003/0191394 A1* | 10/2003 | Simon ................... A61B 6/481 600/473 |
| 2005/0113679 A1 | 5/2005 | Suryanarayanan |

(Continued)

FOREIGN PATENT DOCUMENTS

WO    2009044321 A2    4/2009

OTHER PUBLICATIONS

Brost, A. et al "Respiratory Motion Compensation by Model-Based Catheter Tracking During EP Procedures", Medical Image Analysis, 2010.
(Continued)

*Primary Examiner* — Theodore J Stigell
*Assistant Examiner* — Johnathan Maynard

(57) ABSTRACT

A medical image viewing device for navigation in X-ray imaging includes a processor. The processor is configured to perform a 3D-2D registration of a preoperative three-dimensional volume based on geometry parameters of an image data provider, which provides fluoroscopy images of an object of interest and a plurality of structures with interfering motions to be removed, for creating digitally reconstructed radiograph images of these structures for each fluoroscopy image. These are subtracted from the respective fluoroscopy images to generate structure-suppressed fluoroscopy images free from interfering motions. Based on these structure-suppressed fluoroscopy images, an angiographic image sequence is generated performing a motion estimation of the structures.

13 Claims, 4 Drawing Sheets

(52) U.S. Cl.
CPC .............. *A61B 6/487* (2013.01); *A61B 6/504* (2013.01); *A61B 6/5205* (2013.01); *A61B 6/5241* (2013.01); *A61B 6/5252* (2013.01)

(56) References Cited

U.S. PATENT DOCUMENTS

| | | | |
|---|---|---|---|
| 2005/0220264 A1* | 10/2005 | Homegger | A61B 6/466 378/8 |
| 2008/0025588 A1* | 1/2008 | Zhang | G06K 9/34 382/130 |
| 2008/0101670 A1* | 5/2008 | Baumgart | G06T 5/50 382/128 |
| 2010/0226537 A1* | 9/2010 | Villain | G06T 5/50 382/103 |
| 2011/0164035 A1 | 7/2011 | Liao | |
| 2011/0268333 A1* | 11/2011 | Klingenbeck | A61B 5/0071 382/131 |
| 2012/0163686 A1* | 6/2012 | Liao | G06T 7/33 382/130 |
| 2012/0238871 A1 | 9/2012 | Pfister | |
| 2012/0289826 A1 | 11/2012 | Graumann | |
| 2013/0004052 A1* | 1/2013 | Chen | G06T 11/005 382/132 |
| 2013/0116551 A1 | 5/2013 | Florent | |
| 2013/0172732 A1 | 7/2013 | Kiraly | |
| 2013/0182925 A1* | 7/2013 | Razeto | A61B 6/03 382/131 |
| 2014/0334709 A1* | 11/2014 | Siewerdsen | G06T 7/32 382/132 |

OTHER PUBLICATIONS

Miao, Shun et al "A Hybrid Method for 2-D/3-D Registration between 3-D Volumes and 2-D Angiography for Trans-Catheter Aortic Valve Implantation (TAVI)", Siemens Corporate Research, 2011.

Auvray, Vincent et al "Joint Motion Estimation and Layer Segmentation in Transparent Image Sequences—Application to Noise Reduction in X-Ray Image Sequences." EURASIP Journal on Advances in Signal Processing, 2009.

* cited by examiner

US 10,682,112 B2

SUPPRESSION OF INDEPENDENT MOVEMENTS IN A SERIES OF 2D X-RAY FLUOROSCOPY IMAGES USING A 3D PRE-OPERATIVE VOLUME

CROSS-REFERENCE TO PRIOR APPLICATIONS

This application is the U.S. National Phase application under 35 U.S.C. § 371 of International Application No. PCT/EP2014/074966, filed on Nov. 19, 2014, which claims the benefit of European Patent Application No. 13306585.4, filed on Nov. 20, 2013. These applications are hereby incorporated by reference herein.

FIELD OF THE INVENTION

The present invention relates to medical X-ray imaging, and relates in particular to a medical image viewing device for navigation in X-ray imaging, a medical imaging system, a method for providing improved X-ray image navigation information, as well as to a computer program element and a computer readable medium.

BACKGROUND OF THE INVENTION

For primary diagnosis and treatment of cardiovascular diseases, such as atherosclerosis, ischemia, hypertension and other, interventional cardiology in a cardiac catheterization laboratory are suitable. Cardiac catheterization stands for the insertion of small tubes (catheters) through arteries and/or veins to the myocardium. In order to visualize coronary arteries and cardiac chambers with real-time X-ray imaging, an opaque contrast agent is injected through the catheter. This procedure leads to an image referred to as an angiogram, which is standard for diagnosing cardiovascular disease.

X-ray based cardiac catheterization systems represent the current standard of care and provide imaging modalities for both diagnostic and therapeutic procedures in cardiology. In particular, they are applied for generating real-time images of obstructions to blood flow in the coronary arteries. Real-time X-ray imaging is utilized to guide insertion of balloon-tipped catheters to the point of obstruction, if such is identified, and allows for treatment by angioplasty and stent placement.

Current cardiac catheterization systems enable the majority of minimally invasive procedures in a catheterization laboratory and all have the same fundamental architecture that uses a point X-ray source and a large-area detector. On a monitor, a shadowgram image of the patient is obtained, which is obtained from the detector.

However, during interventions under X-ray guidance, several movements originating from different anatomical structures may be observed in 2D images. The estimation of one particular motion may be affected by others. For example, cardiac motion estimation is impacted by breathing motion and movements of the bones due to the patient's movements. Several techniques, such as transparent motion estimation, decompose 2D X-ray images into regions governed by independent movements.

US 2012/238871 A1 discloses an angiography system with a system control unit that generates a mask image that detects a reference image, effects a registration of the reference image to a C-arm, whereby if necessary a segmentation of the examination object is implemented in the reference image. Image regions lying inside of the segmentation are contrasted in order to generate a mask image, and the mask image from fluoroscopy live images acquired by the angiography system without contrast agent are subtracted in order to form a roadmap image.

SUMMARY OF THE INVENTION

It may thus be an object of the present invention to propose a medical image viewing device and a related method which helps to estimate the motion of structures under consideration for increasing the quality of the obtained digital subtraction angiography (DSA) images.

At this stage it should be noted that all following described aspects of the invention also apply for the medical imaging system, the method for provided improved X-ray navigation, the computer program element, and the computer readable medium.

According to a first aspect of the invention, a medical image viewing device for navigation in X-ray imaging is proposed, the device comprising an image data providing unit, a processing unit, and a display unit. The image data providing unit is configured to provide fluoroscopy images of a region of interest of an object. The processing unit is configured to perform a 3D-2D registration of a preoperative three-dimensional volume based on geometry parameters of the image data providing unit and a plurality of structures to be removed, to create a digitally reconstructed radiograph image of these structures for each fluoroscopy image, to use the digitally reconstructed radiograph images to generate fluoroscopy images free from interfering motions, and to generate an angiographic image sequence based on the fluoroscopy images free from interfering motions under performing a motion estimation of the structure. Further, the display unit is configured to display the angiographic image sequence.

According to an exemplary embodiment, the image data providing unit is configured to provide a sequence of fluoroscopy images through any known and suitable X-ray image acquisition devices. The processing unit is coupled with the image data providing unit and processes the sequence of fluoroscopy images.

Thus, a continuous stream of live images, namely a sequence, representing the current situation is provided, in which sequence the structures under consideration are not shown in the resulting angiogram sequence.

The processing unit of the medical image viewing device preferably takes as input a stream of X-Ray frames delivered by the image data providing unit as well as a preoperatively acquired 3D volume, which should be annotated, and the current geometry parameters of the image data providing unit.

The processing unit is configured to perform a 3D-2D registration based on a plurality of structures to be removed and geometry parameters of the image data providing unit such that a "Digitally Reconstructed Radiograph" (DRR) of these structures is generated. It is ensured that the registration will compensate for the movement of structures under consideration only and the subtraction will suppress the corresponding transparent motions from the angiography image sequences.

To improve the motion estimation of structures under consideration, it is proposed to perform a decomposition of the preoperative 3D volume into regions responsible for independent movements using prior anatomical knowledge from preoperative 3D data. The structures under consideration are registered such that each independent movement is estimated without the others interfering. In a first embodiment, the 3D-2D registration may estimate a rigid transformation for each structure independently. In another embodiment, the 3D-2D registration may be an elastic registration. According to the invention, only undesired structures identified in the 3D volume are used for such a decomposition, resulting in a selective suppression of structures and their corresponding motion in an X-Ray image.

Under the assumption that undesired structures are detected or segmented in an initial 3D volume, such as generated from a CT, an MR or a 3D rotational angiography, a projection of these structures into the actual 2D viewing plane is reconstructed. The 3D-2D registration of the preoperative volume is conducted under consideration of the acquired 2D X-ray images, such that the projection of the structure matches with the 2D X-ray images. The digital reconstruction is subtracted from the images of an X-Ray sequence, which removes the anatomical structure and its specific movement from the sequence. Finally, an improved Digital Subtraction Angiography is computed using these processed X-Ray images.

Different motions and the corresponding structures may be identified at once or in an iterative process. These three-dimensional structures are combined to form a single DRR. The use of a plurality of structures to generate a single DRR allows one to approximate the reconstruction process of the image data providing unit, thus to obtain suppressed-structure fluoroscopy images with intensities similar to the original fluoroscopy images and relevant for subtraction.

Digital Subtraction Angiography (DSA) images are generated by selecting a frame as a reference, which is then subtracted from all the other frames throughout the X-ray image sequence. A DSA is often unable to compensate for complex or composed motions. Motion artifacts may then appear in the resulting subtraction. By localizing and eliminating structures with different motions in the preoperative 3D volume, the estimation of complex motions of interest is clearly improved and thus the quality of subtracted images of the final DSA sequence clearly exceeds the quality of common processes.

In an exemplary embodiment, the processing unit is further configured to identify a suppression area for a partial structure suppression within the fluoroscopy images, to locally suppress structures in the fluoroscopy images in the suppression area and to generate a partly-structure-suppressed fluoroscopy images, i.e. fluoroscopy images that are free of undesired/interfering motion of the suppressed structures in the suppression area. The identification may be conducted through a manual selection of a region of interest, wherein a clinician may simply input desired coordinates through a keyboard or choose delimitations of the regions of interest by means of input devices. The image processing is then limited to the region of interest.

In a still further exemplary embodiment, the processing unit is configured to track a device in the fluoroscopy images and to identify the suppression area based on the position of the tracked device. The device may comprise interventional devices such as guide wires, inserted into a vascular system, and interventional devices, for example delivered via the guide wire to the position to be treated, such as balloons for dilation and stent delivery devices, detachable coils for aneurism clotting, and the like.

In a still further embodiment, the processing unit is configured to create at least one further DRR image of at least one further structure for each fluoroscopy image based on the 3D-2D registration of the preoperative three-dimensional volume based on geometry parameters of the image data providing unit and the at least one further structure to be removed. This supports the consideration of different motions and corresponding structures. To sum up, the processing unit may be adapted for providing one DRR after another, corresponding to further structures. The resulting DRRs may be subtracted from the X-ray images. This may comprise providing a first DRR image of a first structure to be removed from the X-ray images, from a 3D-2D registration of a preoperative 3D volume, subtracting the first DRR images from the X-ray images for generating fluoroscopy images free of undesired/interfering motion of the suppressed structure, providing a further (second) DRR image of a further (second) structure to be removed from the X-ray images, from a 3D-2D registration of a preoperative 3D volume, subtracting the second DRR images from the X-ray images for generating fluoroscopy images free of undesired/interfering motion of the suppressed structure etc.

According to a second aspect of the invention, a medical imaging system is provided that comprises an X-ray image acquisition device and a medical image viewing device according to the above description. The X-ray image acquisition device comprises an X-ray source and an X-ray detector. The X-ray imaging acquisition device is configured to provide X-ray images of an object.

For example, the images used for an angiographic sequence, or an X-ray image used as an angiographic image, are providable by the X-ray image acquisition device, which can also provide a current fluoroscopy image, in which a device is tracked, as mentioned above. In another example, the current fluoroscopy image is provided from the X-ray image acquisition device and the images used for an angiographic sequence, or an X-ray image used as an angiographic image, are provided by another imaging device.

According to a third aspect, a method for providing improved X-ray image navigation information is provided that comprises the steps of a) providing X-ray images of a region of interest of an object, b) providing digitally reconstructed radiograph images of a plurality of structures to be removed from the X-ray images, from a 3D-2D registration of a preoperative 3D volume, c) subtracting the digitally reconstructed radiograph images from the X-ray images for generating structure-suppressed fluoroscopy images, i.e. free of undesired/interfering motion of the suppressed structure, d) generating a DSA sequence through estimating the motion of the structure and subtracting the structure-suppressed fluoroscopy images from the X-ray images under compensation of the motion of the plurality of structures, and e) displaying the DSA sequence.

Different motions and the corresponding structures may be identified at once or in an iterative process, in which one structure after another leads to a corresponding DRR. The resulting DRRs may be subtracted from the X-ray images. In other words, steps b) and c) may be divided in several substeps, which may comprise b') providing a first digitally reconstructed radiograph image of a first structure to be removed from the X-ray images, from a 3D-2D registration of a preoperative 3D volume, c') subtracting the first digitally reconstructed radiograph images from the X-ray images for generating structure-suppressed fluoroscopy images, i.e. free of undesired/interfering motion of the suppressed structure, b") providing a second digitally reconstructed radiograph image of a second structure to be removed from the X-ray images, from a 3D-2D registration of a preoperative 3D volume, c") subtracting the second digitally reconstructed radiograph images from the X-ray images for generating structure-suppressed fluoroscopy images, i.e. free undesired/interfering of motion of the suppressed structure, and so forth.

According to an exemplary embodiment, the method further comprises the steps of identifying a suppression area for a partial structure suppression within the fluoroscopy images, locally suppressing structures in the fluoroscopy images in the suppression area and generating a partly-structure-suppressed fluoroscopy images, i.e. fluoroscopy images that are free of undesired/interfering motion of the suppressed structures in the suppression area.

According to still another exemplary embodiment, the method may comprise the steps of tracking a device in the fluoroscopy images and identifying the suppression area based on the position of the tracked device.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the following drawings.

DETAILED DESCRIPTION OF EMBODIMENTS

Figure 1:
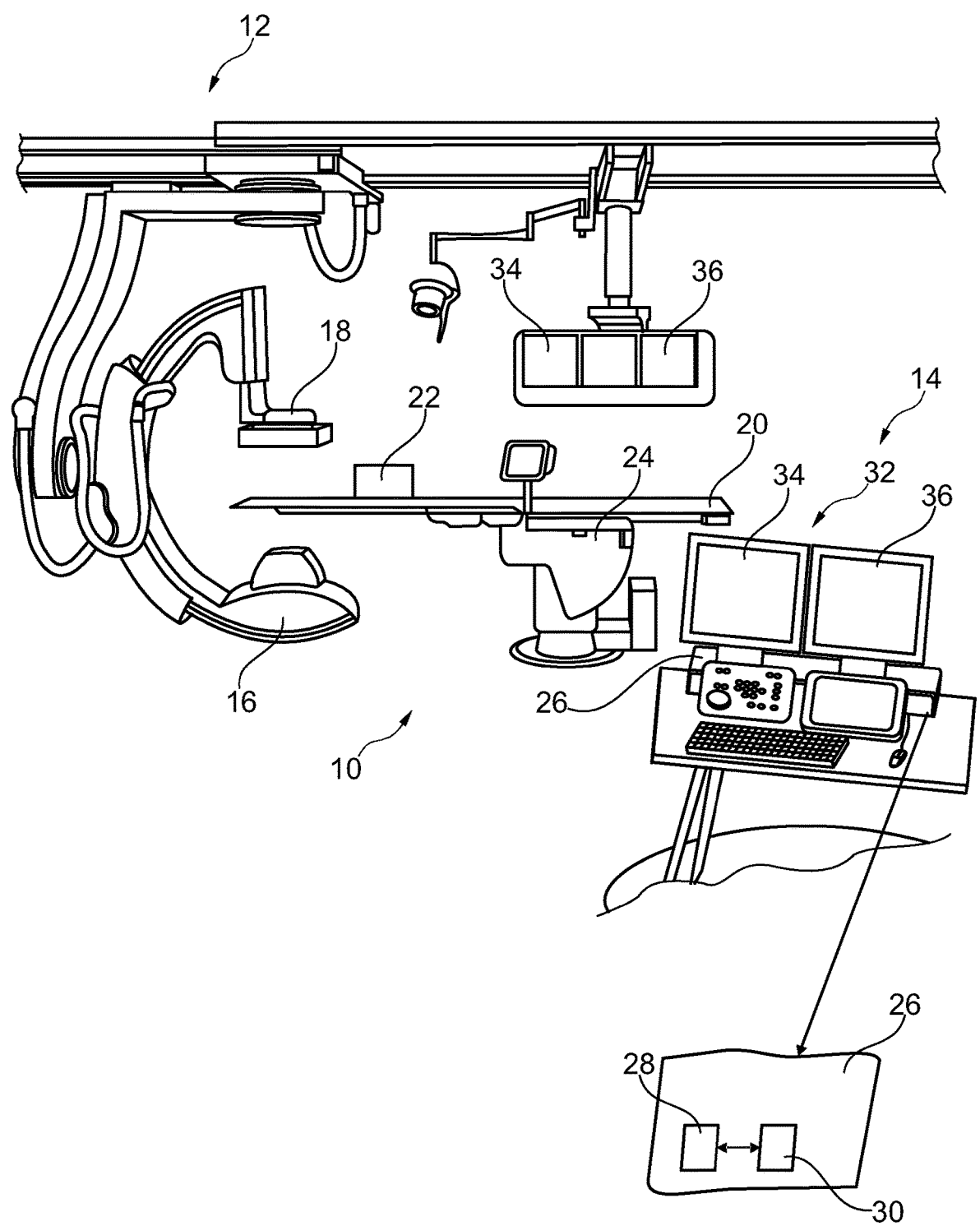
FIG. 1 shows a schematic setup of a medical imaging system with a medical image viewing device for navigation in X-ray imaging in an example.

According to the example of FIG. 1, a medical imaging system 10 is provided, comprising an X-ray image acquisition device 12, and a medical image viewing device 14. The X-ray image acquisition device 12 comprises an X-ray source 16 and an X-ray detector 18. The X-ray image acquisition device 12 is configured to provide X-ray images of an object. Further, a support table 20, for example for receiving an object, such as a patient, is shown, who may receive a contrast agent from a contrast agent injector 22 for introducing a contrast agent into vessels of a patient. A control unit 24 may be present to control the X-ray image acquisition device 12.

It should be noted that the X-ray image acquisition device 12 shown in FIG. 1 is shown as a C-arm structure. However, also other X-ray image acquisition devices, movable or non-movable, may be used without departing from the concept of the invention.

The medical image viewing device 14 exemplarily comprises a calculation unit 26, which inter alia includes an image data providing unit 28 and a processing unit 30. The medical image viewing device 14 also comprises a display unit 32 with a first display 34 and a second display 36, which may also be found at the X-ray image acquisition device 12.

The image data providing unit 28 is configured to provide an angiographic image of a region of interest of an object.

The processing unit 30 is configured to suppress structures in the angiographic image and to generate structure-suppressed images free of undesired/interfering motion of the suppressed structures by using a 3D volume of a selected structure, which is projected onto a desired viewing plane depending on the geometric parameters of the X-ray image acquisition device 12 in order to generate digitally reconstructed radiograph (DRR) images of the selected structure. The processing unit 30 is further configured to subtract these DRR images from the respective fluoroscopy images and let the angiograph image creation be based on these structure-suppressed images free of undesired/interfering motion of the suppressed structures.

The display unit 32 is configured to display suppressed images. The data connection between all components may be provided by wire connection and by wireless connection. Further, the processing unit 30 and the image data providing unit 28 may also be separate devices, not included in a single calculation unit.

In an example, not further shown, the image data providing unit 28 is configured to provide a current fluoroscopy image of the region of interest. The processing unit may be configured to track a device in the fluoroscopy image, to register the fluoroscopy image and the angiographic image, wherein the position of the device may be transferred to the processing unit 30 for further processing.

According to a further example (not further shown), the image data providing unit 28 is configured to provide a sequence of angiographic images and a sequence of fluoroscopy images.

Figure 2A:
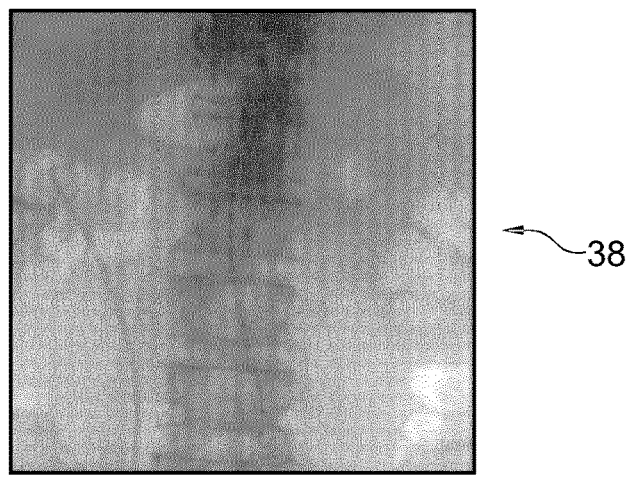
FIGS. 2a to 2c demonstrate motion artefacts without using the method according to the invention.
Figure 2B:
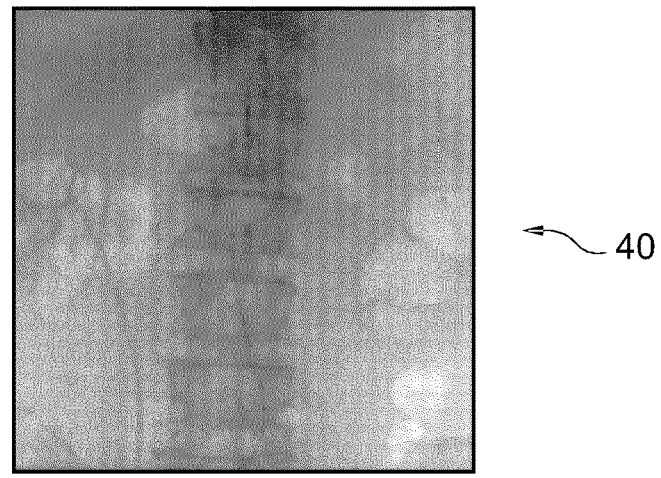
Figure 2C:
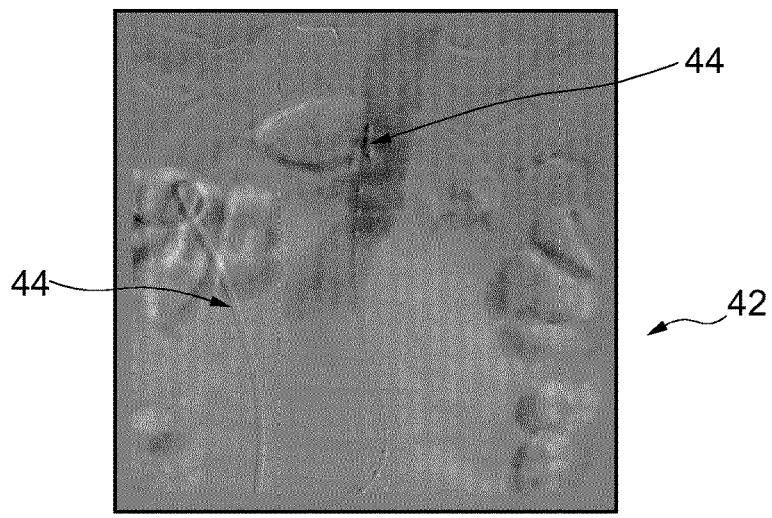

In FIGS. 2a and 2b two different X-ray images 38 and 40, which are acquired at different times. The first image 38 is chosen to be a reference frame for the angiography image creation. Due to a complex motion between the acquisition of both images, a mere subtraction would lead to undesirable artefacts 44, as visible in image 42 of FIG. 2c.

Figure 3:
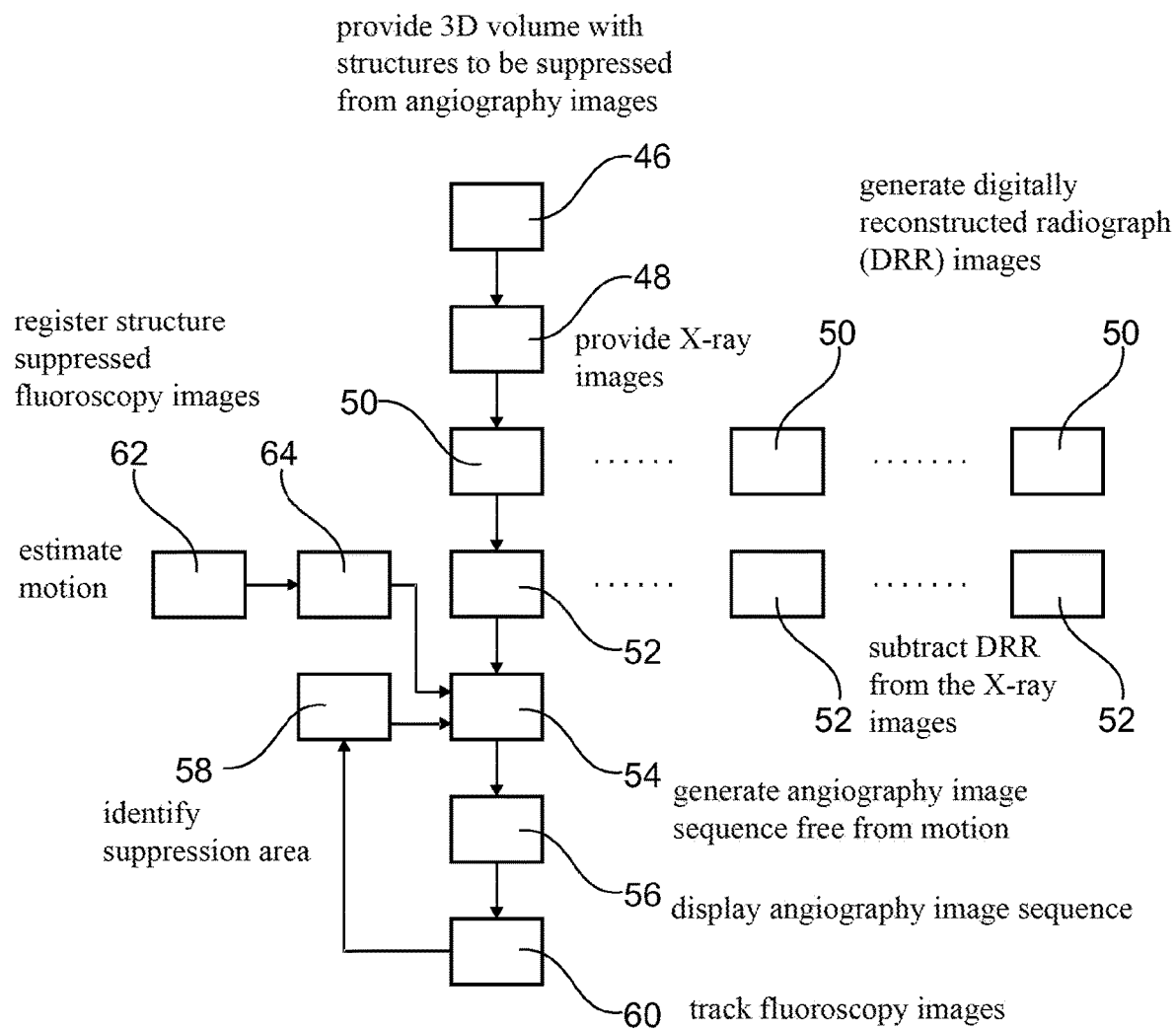
FIG. 3 shows basic steps of an example for a method for providing improved X-ray image navigation information.

However, FIG. 3 shows a method according to the invention, which is able to provide X-ray image navigation information without clear artefacts.

In a first step, a three-dimensional volume comprising a plurality of structures, which are to be suppressed, is provided 46. This volume is a digital representation comprising structures that are to be suppressed from the angiography images. Such a structure may exemplarily be a bone structure. In a further step, X-ray images of a region of interest of an object are provided 48, exemplarily by the X-ray image acquisition device 12 as shown in FIG. 1. Further, digitally reconstructed radiograph images of a 3D-2D registration of the (preoperative) three-dimensional volume of the structures to be removed from the X-ray images is generated 50. This includes the projection of the structures onto the correct viewing plane as well as a registration thereof. Still further, the digitally reconstructed radiograph images are subtracted 52 from the X-ray images for generating structure-suppressed fluoroscopy images free of undesired/interfering motion of the suppressed structures.

Afterwards, an angiography image sequence free from the motion of the plurality of structures is generated 54. Still further, the angiography image sequence is displayed 56, e.g. on the display unit 32 such that the physician receives the necessary information for conduction of the interventional procedure.

It may be helpful to provide the further steps of identifying 58 a suppression area for a partial structure suppression within the fluoroscopy images, locally suppressing structures in the fluoroscopy images in the suppression area, such that step 54 is considered to stand for generating partly-structure-suppressed fluoroscopy images, i.e. fluoroscopy images that are free of undesired/interfering motion of the suppressed structures in the suppression area.

Besides that it may be of use for the physician to gain information about the position of an interventional device. For this purpose, a device in the fluoroscopy images is tracked 60 and identifying 58 a suppression area based on the position of the tracked device.

Figure 4:
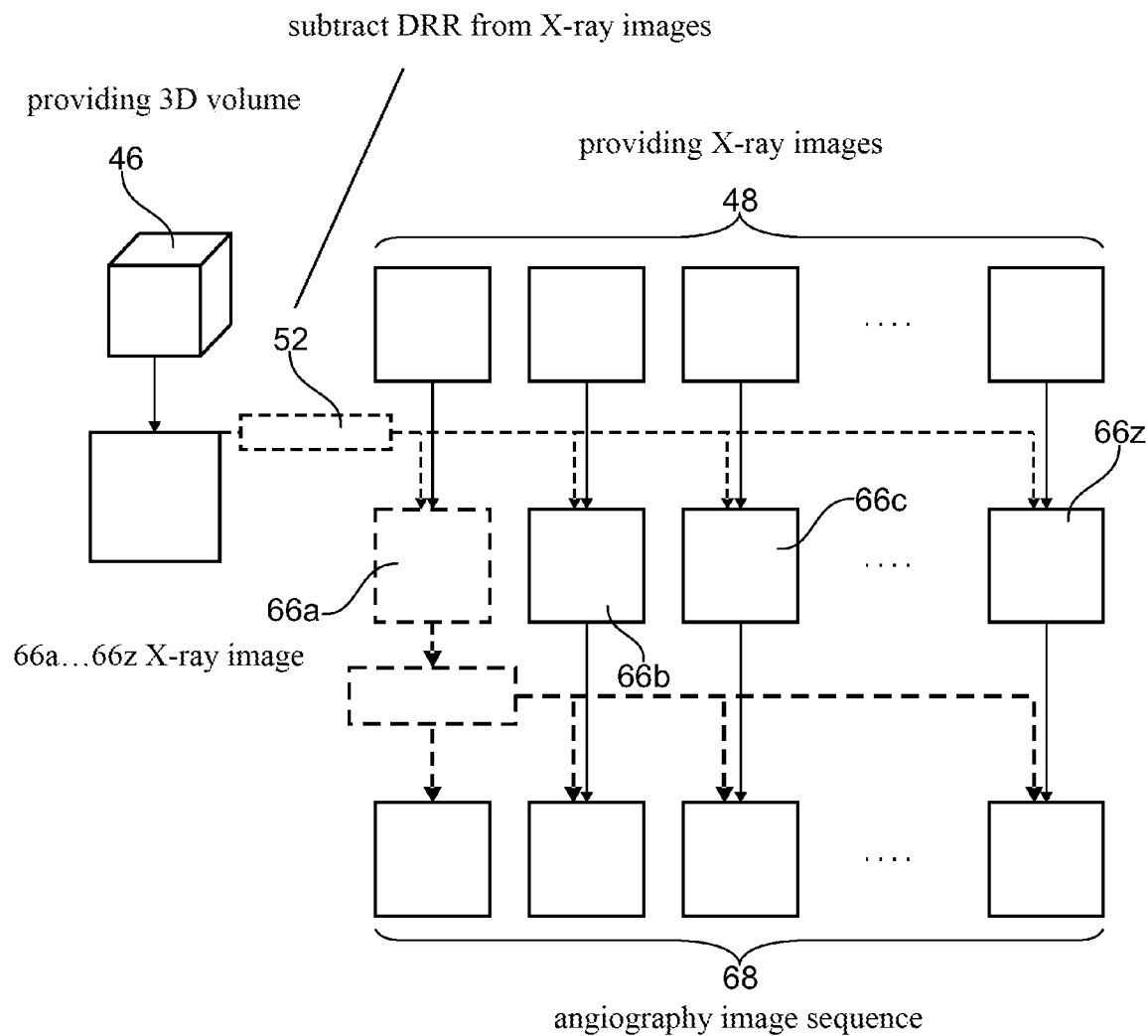
FIG. 4 shows a workflow for the basic steps of FIG. 3.

Finally, FIG. 4 shows a general workflow as proposed according to the invention. A preoperative three-dimensional volume is created 46 and a sequence of X-ray images is acquired 48, from which digitally reconstructed radiography images are subtracted 52. The resulting processed X-ray image sequence comprising X-ray images 66a to 66z is the basis for the angiography image generation. Exemplarily, X-ray image 66a is considered a reference frame, from which subsequently each other X-ray images 66b ... 66z is subtracted, together with a motion estimation. The processes digitally subtracted angiography 68 image sequence results.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

LIST OF REFERENCE SIGNS

10 Medical imaging system
12 X-ray image acquisition device
14 Medical image viewing device
16 X-ray source
18 X-ray detector
20 Support table
22 Contrast agent injector
24 Control unit
26 Calculation unit
28 Image data providing unit
30 Processing unit
32 Display unit
34 First display
36 Second display
38 X-ray image
40 X-ray image
42 Image
44 Artifact
46 Providing three-dimensional volume
48 Providing X-ray images of a region if interest
50 Generating DRR
52 Subtracting DRR from X-ray images
54 Generating angiography image sequence
56 Displaying angiography image sequence
58 Identifying suppression area
60 Tracking device
62 Estimating motion of structure
64 Registering structure suppressed fluoroscopy images
66a ... 66z X-ray image
68 Angiography image sequence

The invention claimed is:
1. A medical image viewing device for navigation in X-ray imaging, comprising:
a fluoroscopy imager configured to provide two-dimensional (2D) fluoroscopy images of a region of interest of an object;

a processor; and a display, wherein the processor is configured to:

perform a decomposition of a preoperative three-dimensional (3D) volume into regions responsible for independent movements that include identified undesired structures to be removed, and wherein the identified undesired structures conduct the independent movements, perform a 3D-2D elastic registration or multiple rigid registrations of the preoperative three-dimensional volume based on geometry parameters of the fluoroscopy imager, based on the decomposition and the 3D-2D elastic registration or the multiple rigid registrations, create a digitally reconstructed radiograph image of the identified undesired structures for each of the 2D fluoroscopy images by projecting the identified undesired structures of the preoperative three-dimensional volume onto a desired viewing plane depending on the geometric parameters of the fluoroscopy imager such that projections of the identified undesired structures match with corresponding structures in the 2D fluoroscopy images, subtract the digitally reconstructed radiograph image from the 2D fluoroscopy images to generate 2D structure-suppressed fluoroscopy images, and generate an angiographic image sequence based on a subtraction of the 2D structure-suppressed fluoroscopy images from a reference image, the angiographic image sequence being free from undesired motion of the identified undesired structures that are suppressed in the 2D structure-suppressed fluoroscopy images, and wherein the display is configured to display the angiographic image sequence.

2. The medical image viewing device according to claim 1, wherein the processor is further configured to identify a suppression area for a partial structure suppression within the 2D fluoroscopy images, to locally suppress a portion of the identified undesired structures in the 2D fluoroscopy images located in the suppression area and to generate 2D partly-structure-suppressed fluoroscopy images.

3. The medical image viewing device according to claim 2, wherein the processor is configured to track a device in the 2D fluoroscopy images and to identify the suppression area based on a position of the tracked device.

4. The medical viewing device according to claim 1, wherein the processor is configured to create at least one further digitally reconstructed radiograph image of at least one further structure for each 2D fluoroscopy image based on the 3D-2D registration of the preoperative three-dimensional volume based on geometry parameters of the image data providing unit and the at least one further structure to be removed.

5. A medical imaging system, comprising:

an X-ray image acquisition device and a medical image viewing device according to claim 1, wherein the X-ray image acquisition device comprises an X-ray source and an X-ray detector and is configured to provide X-ray images of an object.

6. A method for providing X-ray image navigation information, comprising acts of:

providing by an imager two-dimensional (2D) fluoroscopy images of a region of interest of an object;

identifying, in a preoperative three-dimensional (3D) volume, undesired structures to be removed from the 2D fluoroscopy images;

performing by a processor a decomposition of the preoperative 3D volume into regions responsible for independent movements, wherein the preoperative three-dimensional volume includes the identified undesired structures to be removed, and wherein the identified undesired structures conduct the independent movements;

generating a digitally reconstructed radiograph image of the identified undesired structures from a 3D-2D registration of a preoperative 3D volume;

subtracting the digitally reconstructed radiograph image from the 2D fluoroscopy images for generating 2D structure-suppressed fluoroscopy images;

generating an angiography image sequence based on a subtraction of the 2D structure-suppressed fluoroscopy images from a reference image; and displaying the angiography image sequence, wherein the angiography image sequence is free from undesired motion of the identified undesired structures that are suppressed in the 2D structure-suppressed fluoroscopy images.

7. The method of claim 6, further comprising acts of:

identifying a suppression area for a partial structure suppression within the 2D fluoroscopy images;

locally suppressing structures in the 2D fluoroscopy images in the suppression area; and generating 2D partly-structure-suppressed fluoroscopy images.

8. The method of claim 7, further comprising acts of:

tracking a device in the 2D fluoroscopy images to determine a position of the tracked device; and identifying the suppression area based on the position of the tracked device.

9. The method of claim 6, wherein the act of generating the digitally reconstructed radiograph image and the subtracting act comprise act of:

providing first and second digitally reconstructed radiograph images of first and second structures, respectively, to be removed from the 2D fluoroscopy images from the 3D-2D registration of the preoperative 3D volume, and wherein the subtracting act comprise act of:

subtracting the first and second digitally reconstructed radiograph images from the 2D fluoroscopy images for generating the 2D structure-suppressed fluoroscopy images.

10. A non-transitory computer readable medium comprising computer instructions which, when executed by a processor, configure the processor to perform a method for providing X-ray image navigation information, the method comprising the acts of:

providing by an imager two-dimensional (2D) fluoroscopy images of a region of interest of an object;

identifying, in a preoperative three-dimensional (3D) volume, undesired structures to be removed from the 2D fluoroscopy images;

performing a decomposition of the preoperative 3D volume into regions responsible for independent movements, wherein the preoperative three-dimensional volume includes the identified undesired structures to be removed, and wherein the identified undesired structures conduct the independent movements;

generating a digitally reconstructed radiograph image of the identified undesired structures from a 3D-2D registration of a preoperative 3D volume;

subtracting the digitally reconstructed radiograph image from the 2D fluoroscopy images for generating 2D structure-suppressed fluoroscopy images;

generating an angiography image sequence based on a subtraction of the 2D structure-suppressed fluoroscopy images from a reference image; and displaying the angiography image sequence, wherein the angiography image sequence is free from undesired motion of the identified undesired structures that are suppressed in the 2D structure-suppressed fluoroscopy images.

11. The medical image viewing device of claim 1, wherein the independent movements include movements of bones due to movements of a subject.

12. The medical image viewing device of claim 1, wherein the processor is configured to perform the 3D-2D elastic registration or the multiple rigid registrations of the preoperative three-dimensional volume to register each structure of the identified undesired structures to be removed such that each independent movement of the independent movements is estimated without interference from other independent movements of other structures of the identified undesired structures to be removed.

13. The medical image viewing device of claim 1, wherein the processor is configured to perform a registration of the projections of the identified undesired structures and the 2D fluoroscopy images such that the projections of the identified undesired structures match with the corresponding structures in the 2D fluoroscopy images.

* * * * *